(12) United States Patent
Liu et al.

(10) Patent No.: US 8,025,789 B2
(45) Date of Patent: Sep. 27, 2011

(54) ANIONICALLY-CHARGED POLYMER DETECTION METHOD

(75) Inventors: Jianyun Liu, Shanghai (CN); Zhixin Zheng, Shanghai (CN); Yangang Liang, Shanghai (CN); Wei Cai, Shanghai (CN); Su Lu, Shanghai (CN); Li Zhang, Shanghai (CN)

(73) Assignee: General Electric Company, Niskayuna, NY (US)

( * ) Notice: Subject to any disclaimer, the term of this patent is extended or adjusted under 35 U.S.C. 154(b) by 462 days.

(21) Appl. No.: 12/337,228

(22) Filed: Dec. 17, 2008

(65) Prior Publication Data

US 2010/0147707 A1    Jun. 17, 2010

(51) Int. Cl.
*G01N 27/416* (2006.01)
(52) U.S. Cl. .............. 205/787; 205/789; 204/400
(58) Field of Classification Search .............. 204/400; 205/775–794.5
See application file for complete search history.

(56) References Cited

U.S. PATENT DOCUMENTS

| | | | |
|---|---|---|---|
| 4,198,294 A | 4/1980 | Deane | |
| 5,755,939 A | 5/1998 | Dror et al. | |
| 5,807,471 A | 9/1998 | Dror et al. | |
| 6,770,190 B1 | 8/2004 | Milanovski et al. | |
| 2009/0294305 A1* | 12/2009 | Bekki et al. | 205/792 |

FOREIGN PATENT DOCUMENTS

WO    WO 0136542 A1 *   5/2001

OTHER PUBLICATIONS

Copper et al. "Photoelectrochemical Determination of Ascorbic Acid Using Methylene Blue Immobilized in alpha-Zirconium Phosphate" Electroanalysis 1999, 11, No. 17 pp. 1259-1265.*
Ion et al. "Methylene-Blue modified Polypyrrole Film Electrode for Optoelectronic Applications" Journal of Optoelectronics and Advanced Materials Vo. 5, No. 1, Mar. 2003, p. 109-114.*
Dürüst et al., "Determination of Pentosan Polysulfate and Its Binding to Polycationic Species Using Polyion-Sensitive Membrane Electrodes", Analytica Chimica Acta, vol. 432, pp. 253-260, 2001.

* cited by examiner

*Primary Examiner* — Kaj K Olsen
*Assistant Examiner* — Susan Thai
(74) *Attorney, Agent, or Firm* — Mary Louise Gioeni

(57) ABSTRACT

An electrochemical method for measuring the concentration of an anionically-charged and non-electroactive polymer in an aqueous solution is provided. The method comprises immobilizing a cationic dye material on an electrically conductive substrate form a working electrode; contacting the working electrode with the aqueous solution including the anionically-charged and non-electroactive polymer to be measured, and transmitting electrical power to the working electrode; measuring a current of the working electrode under a determined electric potential; and calculating a concentration or quantity of the anionically-charged polymer in the aqueous solution according to the measured current of the working electrode.

15 Claims, 4 Drawing Sheets

ANIONICALLY-CHARGED POLYMER DETECTION METHOD

BACKGROUND

Embodiments of the invention relate generally to methods for detecting polymers in industrial water systems. More particularly, it relates to a method of determining the concentration or availability of anionically-charged polymers in industrial water systems.

Anionically-charged polymers are used for preventing scaling or depositing in industrial water systems, such as a cooling system. The polymers may include polymers derived from unsaturated carboxylates and unsaturated sulphonates and their salts. However, the concentration of the polymers in the industrial water systems must be carefully monitored, because if too little scale-inhibiting polymer is employed, scaling may still occur; while if too much polymer is used, the treatment may not be cost effective. For each given system, there is an optimal concentration level or range that needs to be realized.

Conventional methods of estimating the concentration of the charged polymers employed as scale inhibitors in cooling water include fluorometric methods, turbidity methods, and calorimetric methods. These techniques suffer from a variety of limitations, and simpler, more effective methods of determining the concentration of scale-inhibiting charged polymers would be of substantial value. Thus, there is a need to provide improved systems and methods for measurement of the anionic polymers in aqueous media such as cooling water.

BRIEF DESCRIPTION

One aspect of the invention, a method for measuring anionically-charged and non-electroactive polymer in an aqueous solution is provided. The method comprises immobilizing a cationic dye material on an electrically conductive substrate to form a working electrode; contacting the working electrode with the aqueous solution including the anionically-charged and non-electroactive polymer to be measured, and transmitting electrical power to the working electrode; measuring a current of the working electrode under a determined electric potential; and calculating a concentration or quantity of the anionically-charged polymer in the aqueous solution according to the measured current of the working electrode.

DRAWINGS

In the accompanying drawings like characters represent like parts throughout the drawings, wherein.

DETAILED DESCRIPTION

Figure 1:
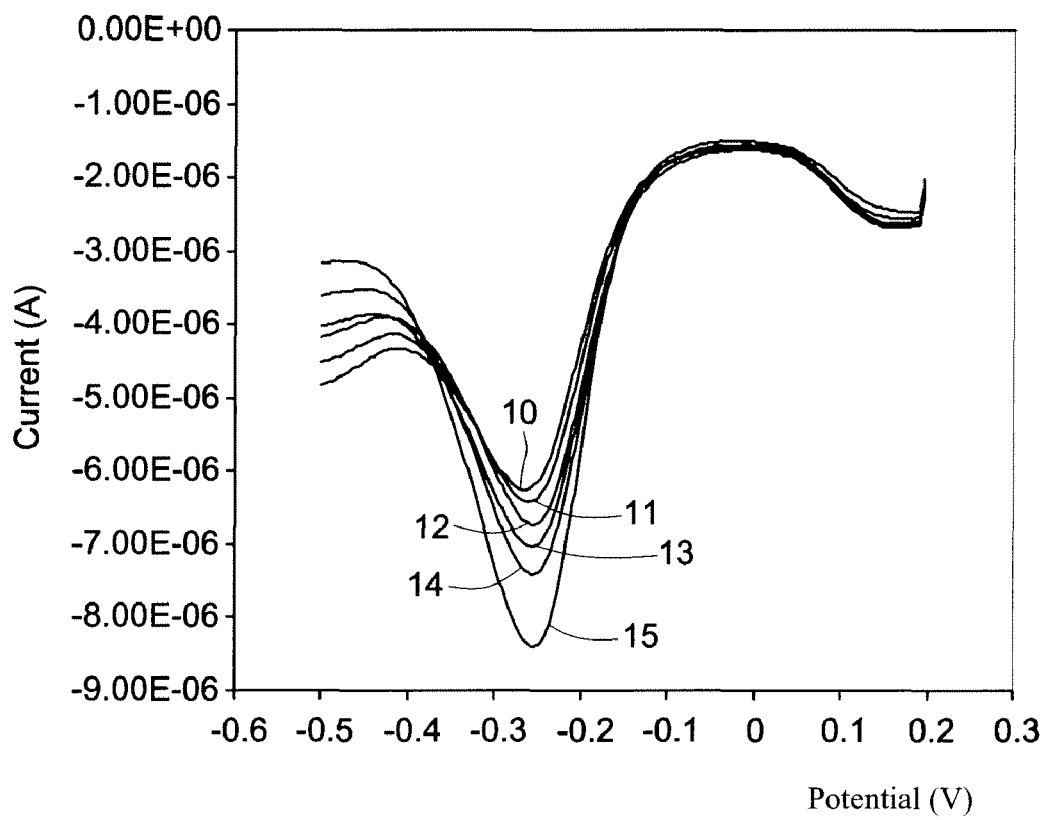
FIG. 1 is a diagram illustrating the relationship of response currents from a working electrode comprising multi-layered Methylene blue (MB) and concentration of anionic polymer HPS-1 in test solutions as measured by a square wave voltammetry method according to one embodiment of the invention.

Embodiments of the invention relate to an electrochemical method for measurement of anionically-charged polymers which are non-electroactive. The anionically-charged polymers are widely used to inhibit scaling in industrial cooling water systems. Suitable anionically-charged and non-electroactive polymers which may be used in industrial cooling water systems, for prevention of scaling, and include, but are not limited to, water-soluble anionic polymers that contain anionic groups. Anionic groups include but are not limited to carboxylate groups, sulfonate groups, sulfate groups, phosphonate groups, and phosphate groups. Examples of the anionically-charged and non-electroactive polymers include polymers comprising structural units derived from acrylic acid, polysufonated polymers, and polymers comprising structural units derived from maleic anhydride. Some specific examples of contemplated anionic polymers are HPS-1, AEC and APES (GE Betz, Trevose, PA.). "Non-electroactive" here means that the polymer will not be oxidized or reduced at a normal electric potential range under a threshold voltage that water begins to electrolyze.

Approximating language, as used herein throughout the specification and claims, may be applied to modify any quantitative representation that could permissibly vary without resulting in a change in the basic function to which it is related. Accordingly, a value modified by a term or terms, such as "about", is not limited to the precise value specified. In at least some instances, the approximating language may correspond to the precision of an instrument for measuring the value. Range limitations may be combined and/or interchanged, and such ranges are identified and include all the sub-ranges included herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about".

As used herein, the terms "comprises," "comprising," "includes," "including," "has," "having" or any other variation thereof, are intended to cover a non-exclusive inclusion. For example, a process, method, article or apparatus that comprises a list of elements is not necessarily limited to only those elements, but may include other elements not expressly listed or inherent to such process, method article or apparatus.

In an exemplary embodiment, an electrochemical device for measurement of an anionically-charged and non-electroactive polymer in an aqueous solution comprises a working electrode having an electrically conductive substrate ("substrate") and a cationic dye material immobilized on an outer surface of the substrate, a counter electrode to form a circuit with the working electrode, the reference electrode to provide steady potential used in measuring the working electrode potential, a power supply device for transmitting a current to the working electrode and the counter electrode, a current sensor for measurement of current of the working electrode, and a processor for calculating a quantity or concentration of the anionic and non-electroactive polymer in the aqueous solution based on the measured current of the working electrode.

In certain embodiments, the substrate may be a column, or a plate, or in a spiral or a wave configuration. The substrate comprises, for example, gold, silver, carbon material, nanocarbon material, or other conductive material as the electrode substrate. In one embodiment, the cationic dye material may comprise, for example, a phenothiazine dye. Phenothiazine dyes are illustrated by methylene blue, dimethyl methylene blue, new methylene blue, basic blue 17, nile blue, indone blue, brilliant cresy blue, netral red, and combinations thereof. In one embodiment, the cationic dye material is a phenothiazine dye selected from the group consisting of methylene blue, dimethyl methylene blue, new methylene blue, and combinations thereof.

In certain embodiments, a method for quantitatively measuring the anionically-charged polymer in an aqueous solution, according to one embodiment of the invention, comprises immobilizing the cationic dye material on the substrate to form the working electrode, contacting the working electrode with the aqueous solution including the anionically-charged polymer to be measured, transmitting electrical power to the working electrode, measuring a response current of the working electrode under a determined potential, and calculating a concentration or quantity of the anionically-charged polymer in the aqueous solution according to the measured response current of the working electrode.

In one embodiment, the substrate is immersed in a dye agent solution to immobilize the cationic dye material and form a cationic dye layer on an outer surface of the substrate. The dye agent solution comprises the cationic dye material, and a supporting electrolyte solution. In one embodiment, the concentration of the dye material in the dye agent solution is in a range from about 0.1 mmol/dm$^3$ to about 0.1 mol/dm$^3$. In another embodiment, the concentration of the dye material in the dye agent solution is in a range from about 0.5 to about 10 mmol/dm$^3$. In yet another embodiment, the concentration of the dye material in the dye agent solution is about 1 mmol/dm$^3$. The supporting electrolyte solution comprises an electrolyte, for example a sodium salt, a potassium salt, or a combination thereof. In one embodiment, the electrolyte in the dye agent solution is at a concentration in a range from about 0.01 mol/dm$^3$ to about 0.5 mol/dm$^3$.

In one specific embodiment, during the process of immobilizing the cationic dye material on the substrate, an electrical potential is applied to the substrate and the cationic dye material in the dye agent solution is electro-polymerized on the substrate to form the cationic dye layer. In one embodiment, the electrical potential applied is in a range from about 0.8 to about 1.2V. In certain embodiments the electrochemical potential required to affect electro-polymerization of the dye agent onto the substrate is dependent on the solution pH. Typically, at higher pH, a higher applied potential is necessary to effect electro-polymerization of the dye agent onto the substrate.

In one embodiment, after the substrate is saturated with the cationic dye material, the substrate, together with the cationic dye layer formed thereon, is immersed into an anionic agent solution. The anionic agent solution comprises a negatively charged polyelectrolyte such as polystyrene sulphonate (PSS), or poly (acrylic acid), to form an anionic layer on the cationic dye layer. The substrate with the dye layer and the anionic layer is again immersed in the dye agent solution. The ionic layer enables the substrate, which is originally saturated with the cationic dye material, to further immobilize more cationic dye material on the anionic layer caused by electrostatic interaction of the cationic dye material with the anionic material. In one embodiment, the substrate is alternately and repeatedly immersed to the dye agent solution and the anionic agent solution to form multiple dye layers on the substrate.

In still another embodiment, process of immobilizing the cationic dye material on the substrate comprising depositing a mixture of polypyrrole and the phenothiazine dye on the substrate. In one embodiment, the dye agent solution which is used to modify the substrate comprises the cationic dye material, a conductive polymer material or a precursor of a conductive polymer, for example pyrrole which is a precursor to polypyrrole (Ppy), and a supporting electrolyte solution. Ppy is cationic and has very good stability and conductivity when immobilized on the substrate, and possesses an additional advantage in that it facilitates adsorption of anionically charged polymers onto the substrate. However, it is difficult to quantify the amount of an anionically-charged and non-electroactive polymer in an aqueous solution to be tested using an electrode modified by Ppy alone using a current difference technique, because Ppy has a weak redox reaction. The cationic dye material is selected such that it has strong interaction with anionic polymer sought to be detected. When the dye agent solution comprises a Ppy precursor a cationic dye material, a Ppy/dye composite film may be formed on the surface of the electrically conductive substrate. In various embodiments, this composite film exhibits good stability and conductivity, and exhibits a strong synergetic interaction with the anionically charged and non-electroactive polymers sought to be detected.

In one embodiment, the concentration of the Ppy precursor in the dye agent solution is in a range from about 10 to about 500 mmol/dm$^3$. In an alternate embodiment, the concentration of the Ppy precursor in the dye agent solution is in a range from about 50 to about 200 mmol/dm$^3$. In yet another embodiment, the concentration of the Ppy precursor in the dye agent solution is about 100 mmol/dm$^3$. In one embodiment, the concentration of the dye material in the dye agent solution is in a range from about 0.2 to about 5 mmol/dm$^3$. In an alternate embodiment, the concentration of the dye material in the dye agent solution is in a range from about 0.5 to about 2 mmol/dm$^3$. In yet another embodiment, the concentration of the dye material in the dye agent solution is about 1 mmol/dm$^3$. In one embodiment, the ratio of the concentration of the cationic dye material to the concentration of the Ppy precursor in the dye agent solution is in a range from about 1/500 to about 1/10. In an alternate embodiment, the ratio of the concentration of the cationic dye material to the concentration of the Ppy precursor in the dye agent solution is in a range from about 1/200 to about 1/50. In yet another embodiment, the ratio of the concentration of the cationic dye material to the concentration of the Ppy precursor in the dye agent solution is about 1/100. In one embodiment, the concentration of the electrolyte in the dye agent solution is below 10 mmol/dm$^3$. In another embodiment, the concentration of the electrolyte in the dye agent solution is below 5 mmol/dm$^3$. In yet another embodiment, the concentration of the electrolyte in the dye agent solution is below 1 mmol/dm$^3$. In certain embodiments, the concentration of the electrolyte in the dye agent solution may be used to control uniform growth of the composite film on the substrate and the rate of formation of the composite film on the substrate.

In one embodiment, the method for measuring the concentration of an anionically charged and non-electroactive polymer in an aqueous solution further comprises defining a calibration curve for each polymer of interest. In one embodiment, a calibration curve is generated by preparing aqueous sample solutions containing known amounts of polymer, contacting each solution with the working electrode and applying a series of electrical potentials while measuring resultant response currents. In this way a plurality of curves is obtained (for example the family of curves shown in FIG. 1), each curve corresponding to a different concentration of the polymer. In one embodiment, the calibration curve is defined by selecting one electrical potential in the scanned potential range, and obtaining a plurality of current values for each concentration. In one embodiment, the calibration curve is a plot of current vs. the known concentrations. In one embodiment, calibration curve is approximated as a linear trend.

In one embodiment, a two-electrode system is used in the process of defining the calibration curve, which comprises the working electrode and a counter electrode both immersed into the sample of the aqueous solution. And thus the scanned electrical potential is applied between the working electrode and counter electrode by a power supply device. In another embodiment, a three-electrode system is used in the process used to prepare the calibration curve. In one embodiment, the three-electrode system comprises the working electrode, the counter electrode, and a reference electrode. The reference electrode is energized with a steady electrochemical potential, and thus reaction potentials of the working electrode can be accurately measured.

After the calibration curve is defined, the working electrode is immersed in the aqueous solution to be measured. The two-electrode system or three-electrode system as described above is used. The measured response current of the working electrode is mapped to the calibration curve, and the concentration or quantity of the anionically charged polymer in the aqueous solution is obtained.

EXAMPLES

In the examples illustrated below, the substrate of the working electrode is selected from Au, graphite, or glassy carbon materials. The counter electrode and the reference electrode are respectively coiled Pt wire and an Ag/AgCl (1M KCl) electrode. The dye agent solution and anionic solutions are all prepared using deionized Milli-Q water (Millipore).

Example 1

Methylene blue (MB) is selected as the cationic dye material, a gold electrode is selected as the substrate for the working electrode, and the polymer to be detected is HPS-1 (acrylic acid/1-allyoxy, 2-hydroxypropylsulfonate). The dye agent solution for immobilizing MB on the gold electrode comprises NaCl solution as the supporting electrolyte solution with a concentration of $0.1M/dm^3$ and MB with a concentration of 1 $mmol/dm^3$. A self-assembled monolayer (SAM) of mercapt-propionic acid (MPA) introduces a carboxyl group to the gold surface which, on further reaction with MB by electrostatic interaction. MB is adsorbed on the gold electrode to form a MB layer on the gold electrode after about 10 minutes.

After the gold electrode is saturated with MB, the gold electrode with a MB layer is immersed into the anionic agent solution, which comprises poly (styrene-sulphonate) (PSS) to form an anionic layer on the gold electrode after about 10 minutes. The gold electrode is further immersed to the dye agent solution with MB, more MB is adsorbed on the gold electrode by the electrostatic interaction of the anionic layer with MB. In this example, the gold electrode is alternatively immersed to the dye agent solution and the anionic agent solution to form four MB layers on the gold electrode to provide a working electrode.

Referring to FIG. 1, the working electrode is immersed in the test aqueous solution to build a calibration curve. Response currents of the working electrode to different HPS-1 concentrations are measured by square wave voltammetry, wherein U/A curves 10-15 respectively represent HPS-1 concentrations of 0, 4, 8, 20, 30 and 40 ppm. Each of the U/A curves has a peak current and the peak current decreases gradually as concentration of the HPS-1 increases, indicating the interaction of MB and HPS-1, which reduces the redox current of the MB on the working electrode.

Figure 2:
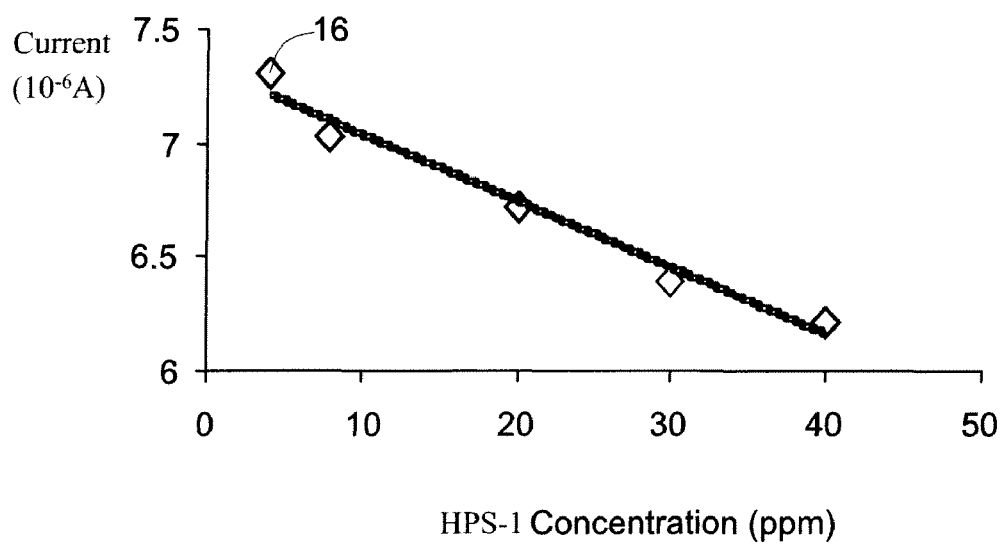
FIG. 2 illustrates a calibration curve defined by the diagram of FIG. 1.

Referring to FIG. 2, a calibration curve is built according to FIG. 1 by selecting a determined potential which corresponds to peak current of each U/A curves 10-15, and recording the corresponding currents of different HPS-1 concentrations under the determined potential to provide a plurality of points 16. As is illustrated in FIG. 2, the relationship of the reduced current to HPS-1 concentration is substantially linear.

Example 2

MB is selected as the cationic dye material, a mercapt-propionic acid modified Au electrode is selected as the substrate for the working electrode, and the polymer to be detected is HPS-1. The dye agent solution for immobilizing MB on the graphite electrode comprises 0.1M phosphate buffer solution, 0.1M KCl and 0.4 mM MB. During the immobilization process, a 1.2V potential is applied to the Au electrode for about five minutes, and the MB is deposited on the Au electrode under the influence of the applied potential to form a working electrode.

Figure 3:
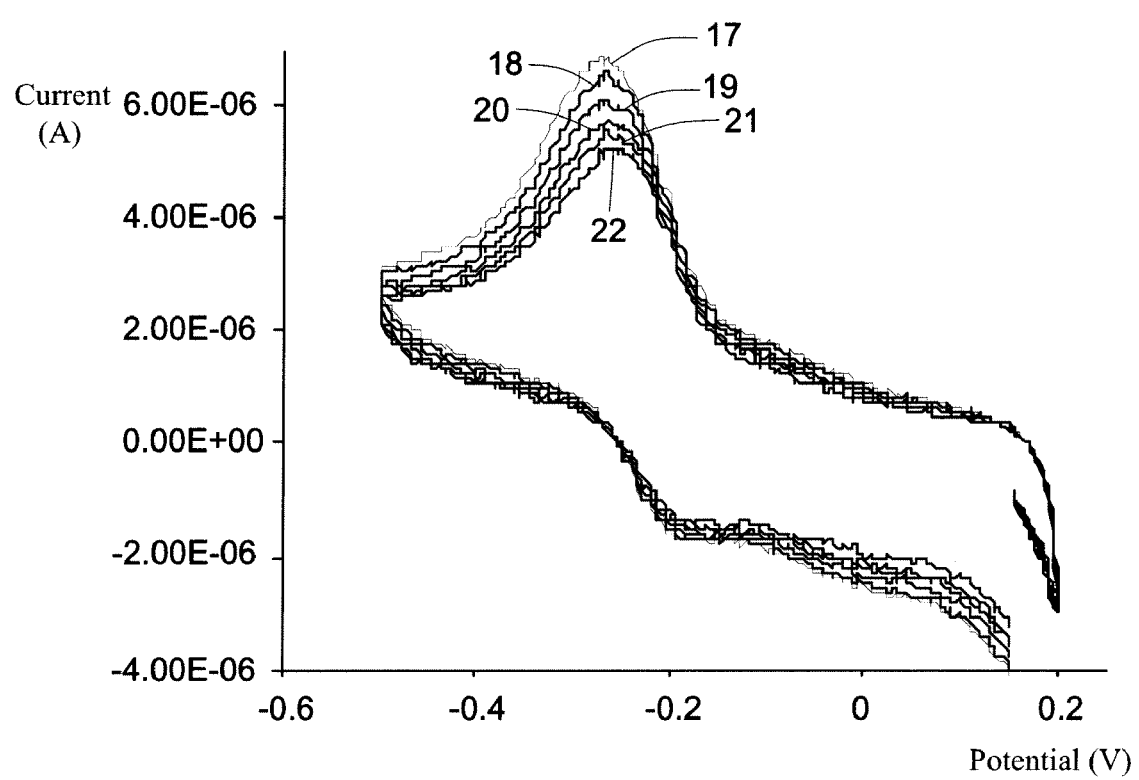
FIG. 3 is a diagram illustrating the relationship of response currents from a working electrode with a MB layer produced by an electro-polymerized method and concentration of anionic polymer HPS-1 measured by a cyclic voltammetry method according to another example.

Referring to FIG. 3, the working electrode is immersed to a series of aqueous test solutions to build a calibration curve. Response currents of the working electrode to different HPS-1 concentrations are measured by cyclic voltammetry at a 10 mV/s scan rate, in a potential range between −0.4V and 1.2V. As illustrated, U/A curves 17-22 respectively represent HPS-1 concentrations in the test solutions of 0, 12.5, 37.5, 50, and 75 ppm. Each of the U/A curves has a peak current, and the peak current decreases gradually as the concentration of the HPS-1 increases, indicating the interaction of MB and HPS-1, which reduces the redox current of the MB on the working electrode.

Figure 4:
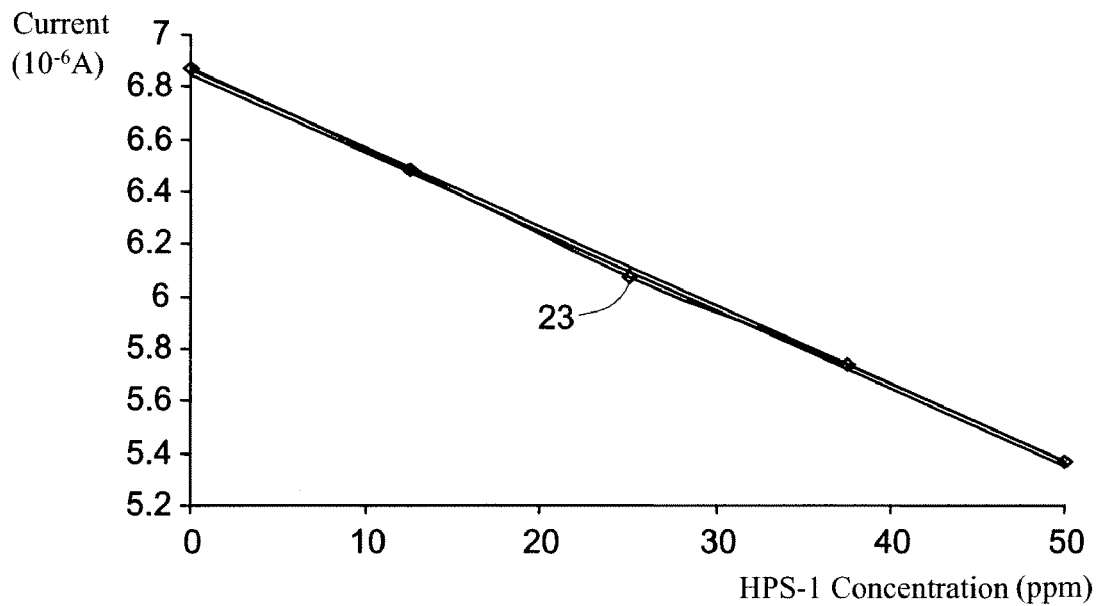
FIG. 4 illustrates a calibration curve defined by the diagram of FIG. 3.

Referring to FIG. 4, a calibration curve is built using the data shown in FIG. 3 by selecting a determined potential which corresponds to the peak current of each U/A curve, and recording the corresponding currents of different HPS-1 concentrations under the determined potential to provide a plurality of points 23. As is illustrated, the relationship between the reduced current and HPS-1 concentration is substantially linear.

Example 3

MB is selected as the cationic dye material, a glassy carbon electrode is selected as the substrate for the working electrode, and the polymer to be detected is HPS-1. The dye agent solution for immobilizing MB on the carbon electrode comprises 0.1M pyrrole, and 1 mM NaCl. 1 mM MB is added during the polymerization to obtain a Ppy/dye composite layer on the glassy carbon electrode by applying a constant potential at 0.8V for about ten minutes to provide a working electrode.

Figure 5:
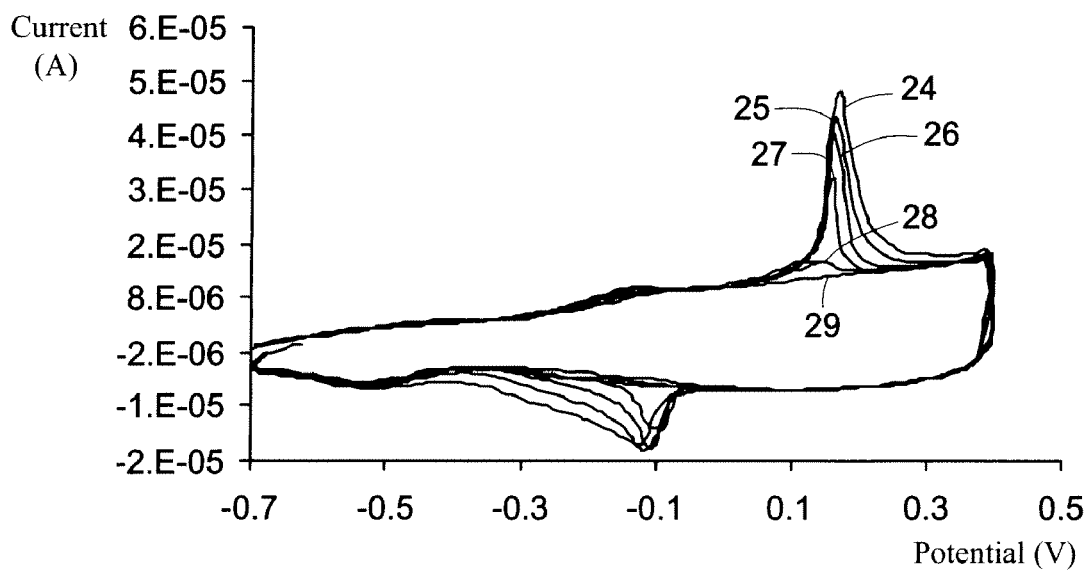
FIG. 5 is a diagram illustrating the relationship of response currents from a working electrode with an MB/Ppy composite layer and concentration of anionic polymer HPS-1 measured by a cyclic voltammetry method according to still another example.

Referring to FIG. 5, the working electrode is immersed to a series of aqueous test solutions to build a calibration curve. Response currents of the working electrode to different HPS-1 concentrations are measured by cyclic voltammetry. As illustrated, U/A curves 24-29 respectively represent HPS-1 concentrations of 0, 2.5, 5, 10, 15, 22.5, and 32.5 ppm. Each of the U/A curves has a peak current at about 0.2V and the peak currents increase gradually as concentration of the HPS-1 concentration increases. Since the anionically charged polymer (the concentration which is sought to be determined) is non-electroactive, the new peak appearance and its corresponding change in peak current observed in each case is attributable to the strong adsorption of HPS-1 onto the composite Ppy/MB layer, and thus the measured response currents are adsorption currents. Such adsorption behavior is facilitated by electrostatic interactions between the negatively charged HPS-1 and the positively charged PPy/MB composite layer on the surface of the working electrode.

As illustrated, the peak current in each curve appears at about 0.2V which is in a very suitable potential window to diminish the effect of many electroactive interferences during detection of the polymer in the aqueous solution.

Figure 6:
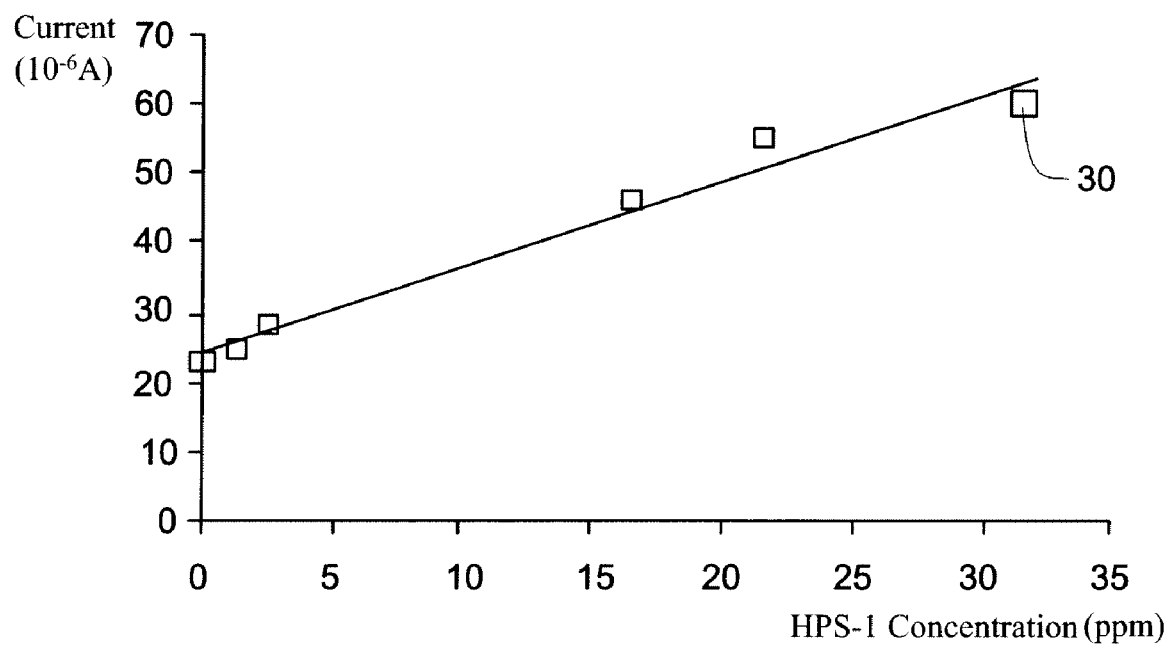
FIG. 6 illustrates a calibration curve defined by the diagram of FIG. 5.

Referring to FIG. 6, a calibration curve is built using the data provided in FIG. 5 by selecting a determined potential which corresponds to the peak current of each U/A curve, and plotting the corresponding currents versus HPS-1 concentrations under the determined potential to provide a plurality of points 30. As is illustrated, the relationship between current and HPS-1 concentration is substantially linear, in a concentration range of from 1 to 30 ppm. The method described in this example is especially suitable for determining the concentration of HPS-1 in cooling water since a concentration of about 20 ppm HPS-1 is typical for many scale inhibition applications of HPS-1 in cooling water system.

The embodiments described herein are examples of articles, systems and methods having elements corresponding to the elements of the invention recited in the claims. This written description enables those of ordinary skill in the art to make and use embodiments having alternative elements that likewise correspond to the elements of the invention recited in the claims. The scope of the invention thus includes articles, systems and methods that do not differ from the literal language of the claims, and further includes other articles, systems and methods with insubstantial from the literal language of the claims. While only certain features and embodiments have been illustrated and described herein, many modifications and changes may occur to one of ordinary skill in the relevant art. The appended claims cover all such modifications and changes.

The invention claimed is:

1. A method for measuring anionically-charged and non-electroactive polymer in an aqueous solution, comprising:
   immobilizing a cationic dye material on an electrically conductive substrate to form a working electrode;
   contacting the working electrode with the aqueous solution including the anionically-charged and non-electroactive polymer to be measured, and transmitting electrical power to the working electrode;
   measuring a current of the working electrode under a determined electric potential; and
   calculating a concentration of the anionically-charged polymer in the aqueous solution according to the measured current of the working electrode.

2. The method of claim 1, wherein the electrically conductive substrate comprises gold, silver, carbon, nano-carbon material, glassy carbon, or a combination thereof.

3. The method of claim 1 further comprising contacting the working electrode to a test solution to be measured, and forming a linear calibration curve for the polymer to be detected which represents a response current due to the concentration change of the polymer in the test solution.

4. The method of claim 3, wherein disposing the working electrode in a test solution to be measured comprises preparing the test solution comprising an electrolyte, and wherein forming a linear calibration curve comprises increasing the concentration of the polymer in the test solution and recording corresponding response current of the working electrode under a determined electric potential.

5. The method of claim 4, wherein the electrolyte comprises a sodium salt, a potassium salt, or a combination thereof, and wherein a concentration of the electrolyte is in a range from about 0.01 to about 0.5 mole/dm$^3$.

6. The method of claim 1, wherein immobilizing a cationic dye material on an electrically conductive substrate comprises disposing the electrically conductive substrate into a dye agent solution, and physically adsorbing a cationic dye material in the dye agent solution on a surface of the electrically conductive substrate to form a cationic dye layer on the substrate.

7. The method of claim 6, wherein immobilizing an electrically conductive substrate with a cationic dye material further comprises disposing the substrate with the cationic dye layer into an anionic agent solution comprising an anionic material, and physically adsorbing the anionic material on the cationic dye layer to form an anionic layer on the cationic dye layer.

8. The method of claim 7, wherein immobilizing an electrically conductive substrate with a cationic dye material further comprises alternately contacting the substrate with the dye agent solution and the anionic agent solution to form multiple dye layers.

9. The method of claim 1, wherein immobilizing an electrically conductive substrate with a cationic dye material comprises disposing the electrically conductive substrate into a dye agent solution, and applying an electrical potential to the substrate thereby depositing a cationic dye material on the substrate.

10. The method of claim 1, wherein the cationic dye material is a phenothiazine dye selected from the group consisting of methylene blue, dimethyl methylene blue, new methylene blue, basic blue 17, nile blue, indone blue, brilliant cresy blue, netral red, and combinations thereof.

11. The method claim 1, wherein the cationic dye material comprises methylene blue, and wherein measuring a current of the working electrode under a determined electric potential comprises measuring a redox current of methylene blue.

12. The method of claim 1, wherein immobilizing an electrically conductive substrate with a cationic dye material comprises contacting the electrically conductive substrate with a dye agent solution which comprises pyrrole monomer and a phenothiazine dye, and electropolymerizing the pyrrole monomer to polypyrrole and depositing a mixture of polypyrrole and the phenothiazine dye on the substrate.

13. The method of claim 12, wherein a concentration of the phenothiazine dye in the dye agent solution is in a range from about 0.1 and about 5 milli-mole/dm$^3$.

14. The method of claim 12, wherein a concentration of the pyrrole monomer in the dye agent solution is in a range from about 50 to about 500 milli-mole/dm$^3$.

15. The method of claim 12, wherein measuring a current of the working electrode under a determined electric potential comprises measuring an adsorption current of the working electrode.

* * * * *